United States Patent [19]

Wakeman et al.

[11] 4,058,488
[45] * Nov. 15, 1977

[54] IMIDAZOLINE OXIDES

[75] Inventors: Reginald L. Wakeman, Paris, France; Zdzislaw W. Dudzinski, Clifton; Arnold Lada, Montclair, both of N.J.

[73] Assignee: Millmaster Onyx Corporation, New York, N.Y.

[*] Notice: The portion of the term of this patent subsequent to Apr. 20, 1993, has been disclaimed.

[21] Appl. No.: 614,173

[22] Filed: Sept. 17, 1975

Related U.S. Application Data

[63] Continuation-in-part of Ser. No. 201,573, Nov. 23, 1971, Pat. No. 3,951,878, which is a continuation-in-part of Ser. No. 804,669, March 5, 1969, abandoned, which is a continuation-in-part of Ser. No. 562,522, July 5, 1966, abandoned.

[51] Int. Cl.² .............................................. C11D 1/58
[52] U.S. Cl. .................................... 252/542; 252/106; 252/524; 252/529; 252/547; 252/548; 548/337
[58] Field of Search ............... 252/542, 529, 547, 548, 252/524, 106, DIG. 1, DIG. 13; 260/309.6

[56] References Cited

U.S. PATENT DOCUMENTS

| | | | |
|---|---|---|---|
| 3,098,794 | 7/1963 | Dohr et al. | 8/10.1 |
| 3,156,656 | 11/1964 | Libby | 252/542 |
| 3,202,714 | 8/1965 | Zimmerer et al. | 252/547 X |
| 3,206,512 | 9/1965 | Koebner et al. | 260/583 X |
| 3,607,765 | 9/1971 | Wixon | 252/524 |
| 3,951,878 | 4/1976 | Wakeman et al. | 252/542 |

*Primary Examiner*—Thomas J. Herbert, Jr.
*Attorney, Agent, or Firm*—Arthur A. Jacobs

[57] ABSTRACT

A surface-active composition consisting essentially of (a) a compound having the structure:

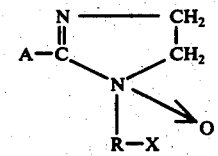

wherein A is either coco or tallow, R is either $C_2H_4$ or $C_3H_6$ and X is either OH or $NH_2$, and wherein the arrow indicates a semi-polar bond, and (b) another surface-active agent selected from the group consisting of anionic, cationic and non-ionic surface active agents.

4 Claims, No Drawings

IMIDAZOLINE OXIDES

This is a continuation-in-part of application Ser. No. 201,573, filed Nov. 23, 1971, now issued as U.S. Pat. No. 3,951,878, dated Apr. 20, 1976, which is a continuation-in-part of application Ser. No. 804,669, filed Mar. 5, 1969, now abandoned which is, in turn a continuation-in-part of application Ser. No. 562,522, filed July 5, 1966 now abandoned.

This invention relates to amine oxides having surfaceactive and other desirable properties, and it more particularly relates to alkenyl imidazoline oxides.

In accordance with the present invention, highly effective detergent, cosmetic and other compositions are formed with the inclusion of oxides of alkenyl-2-imidazolines having the structural formula:

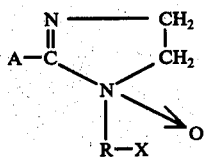

wherein A is either coco or tallow, R is either $C_2H_4$ or $C_3H_6$ and X is either OH or $NH_2$, and wherein the arrow indicates a semi-polar bond.

These 2-imidazolines may be prepared by condensing the particular fatty acid with diethylene triamine ($NH_2C_2H_4NHC_2H_4NH_2$) or aminoethyl ethanolamine ($NH_2CH_2CH_2NHCH_2CH_2OH$) by standard procedures, whereby two molecules of water are eliminated. Such techniques include azeotropic distillation with a suitable solvent, or heating under reduced pressure or in a stream of inert gas. Thereafter, unreacted amine may be stripped off from the reaction mass, leaving a product which consists essentially of 2-substituted-imidazoline having either an aminoethyl or hydroxyethyl substituent on the 1-nitrogen atom.

The imidazolines obtained in this manner may then be oxidized by treatment with a suitable oxidizing agent, such as hydrogen peroxide, an organic peroxide, or ozone, to produce the desired 2-substituted imidazoline oxides. Oxidation processes of this type are well-known in the art. In general, it is preferred to use hydrogen peroxide.

The following examples are illustrative of the procedures involved, but are not intended to limit the invention except as claimed.

EXAMPLE 1

A glass-lined kettle fitted with an agitator, a condenser, a phase separator and solvent return, a receiver, and a source of vaccum, was charged with 1000 grams of stripped coco fatty acids (est. 4.42 moles), 550 grams of aminoethyl ethanolamine (about 5.3 moles) and 140 grams of toluene.

The kettle and its auxiliaries were purged with nitrogen, and the mixture was heated while being agitated. At about 125° C, distillation began, at which time the nitrogen was cut off from the pot and switched to the vent of the condenser. Water and toluene distilled azeotropically, and the toluene was returned to the reactor. The reaction proceeded for about 2 to 3 hours, during which hours the temperature rose to about 175°–195° C.

At this point a partial vaccum was applied, and both water and toluene were stripped off the charge. When distillation appeared complete, the receiver was disconnected from the apparatus, and full vaccum was applied gradually, to about 5–10 mm. pressure, and to a pot temperature of 200° C, to remove excess aminoethyl ethanolamine.

The yield of 2-substituted-1-hydroxyethyl-imidazoline was 1140 grams, about 88% of theory; and about 10–12% of the yield was 2-heptadecenyl-1-hydroxyethyl-imidazoline.

EXAMPLE 2

The process used in Example 1 was repeated except that, instead of the coco fatty acids, 175 lbs. of tallow fatty acids (est. 0.63 lb. moles) were used. The other reactants used were 78 lbs. aminoethyl ethanolamine (about 0.75 lb. moles) and 25 lbs. toluene.

The yield of 2-substituted-1-hydroxyethyl-imidazoline was 218 ½ lbs., about 91% of theory; and about 50% of the yield was 2-heptadecenyl-1-hydroxyethyl-imidazoline.

EXAMPLE 3

903 grams (about 3 moles) of the product of Example 1 was charged, along with 350 lbs. of isopropanol into a round-bottom flask fitted with an agitator, a reflux condenser, a dropping funnel and an immersion bath for cooling and heating.

The dropping funnel was charged with 315 grams of 34% hydrogen peroxide (about 31.5 moles). The charge was maintained at 37° C during the gradual addition of the hydrogen peroxide over a period of 45 minutes. The reaction was exothermic and, on completion of the addition, the temperature fell. Agitation was continued for an additional short period to insure completion of the oxidation. 125 grams of distilled water was then added, with continued agitation, to yield 1500 grams of a solution containing about 60% of active solids in the form of 2-substituted-1-hydroxyethyl-1-imidazoline oxide. About 10–12% of these solids was 2-hetadecenyl-1-hydroxyethyl-1-imidazoline oxide.

Coco fatty acids have the following approximate composition by weight: $C_8$ — 6%; $C_{10}$ — 7%; $C_{12}$ — 47%; $C_{14}$ — 18%; $C_{16}$ — 8%; $C_{18}$ — 2%; $C_{18}$ (unsaturated oleyl) — 10%.

Tallow fatty acids have the following approximate composition by weight: $C_{16}$ — 26%; $C_{18}$ — 14%; $C_{18}$ (unsaturated oleyl)— 49%; $C_{14}$ — 4%; $C_{18}$ (unsaturated linoleic) — 6%.

While a most satisfactory product is obtained at the above-noted temperature of 37° C, it is not necessary to restrict the reaction to such temperature. Any temperature from about 25° C to about 100° C may be used, although the color of the product darkens as the temperature rises, while temperature control by cooling becomes increasingly difficult at low temperatures. Furthermore, although isopropanol is used in this and the following examples, other polar solvents such as ethanol, methanol, or the like, may be substituted. The alcohol serves as a diluent to facilitate heat transfer and to keep the viscosity within workable range.

It is also not essential in these examples to add water during the reaction. On the other hand, the reaction may be conducted in water alone although this involves generally undesirable foaming and an indefinite induction period.

Generally, oxidation occurs at the 1-nitrogen. However, by employing a larger excess of hydrogen peroxide, some further oxidation takes place. The additional oxidation is believed to occur at the 3-nitrogen.

EXAMPLE 4

The process used in Example 3 was repeated, using 140 grams (about 0.5 moles) of the product of Example 2, the other reactants being 60 grams of isopropanol, 55 grams of 34% hydrogen peroxide (about 0.53 moles) and 25 grams of distilled water.

The product obtained was 2-substituted-1-hydroxyethyl-1-imidazoline oxide; and about 50% of the product was 2-heptadecenyl-1-hydroxyethyl-1-imidazoline oxide.

The aforesaid imidazoline oxides are useful surface-active agents. As such they may be employed as components of dishwashing compounds and light- and heavy-duty detergent compositions and the like, as well as such cosmetic formulations as shampoos, creams, and lotions. They may be formulated compatibly with anion-active, cation-active and non-ionic agents at controlled acidities. They also impart disinfecting or sanitizing properties, since they are bactericidal and fungicidal.

Anionic synthetic surface-active agents (surfactants) are generally described as those compounds which contain both hydrophilic and lyophilic groups in their molecular structure and ionize in an aqueous medium to give anions containing both the lyophilic group and hydrophilic group. The class of surfactants particularly useful in the practice of this invention are those classified as detersive surfactants.

Illustrative of the preferred anionic surfactants used to practice this invention are the alkyl aryl sulfonates, the alkyl sulfates, alkyl ether sulfates and mixtures thereof.

Compounds illustrative of the alkyl aryl sulfonates useful in the practice of this invention include monoethanolammonium dodecylbenzene sulfonate; triisopropanolammonium tricosyl benzene sulfonate; diisobutanolammonium dodecylbenzene sulfonate; 1-n-decanolammonium octyl benzene sulfonate, triethanolammonium nonylbenzene sulfonate; triisopropanolammonium dodecylnaphthalene sulfonate; monoethanolammonium heptadecylbenzene sulfonate; ammonium eicosyl naphthalene sulfonate; ethanolammonium undecyl naphthalene sulfonate; triethanolammonium dodecyl benzene sulfonate; ethanolammonium tetradecyl benzene sulfonate; ammonium octadecyl benzene sulfonate; triisopropanolammonium decylbenzene sulfonate; ammonium pentadecyl benzene sulfonate as well as the corresponding alkali metal (i.e. sodium and potassium) salts of these and other sulfonates. The preferred alkyl sulfates useful in the practice of this invention are those represented by the general formula:

where M is either an alkali metal, such as sodium or potassium, or ammonium, or an alkanol ammonium radical represented by the following formula:

where $n$ is an integer from 1 to 4, $m$ is an integer from 0 to 3 and $m+n$ equals 4, and R is an alkanol radical.

Compounds illustrative of the above alkyl sulfate class include triisopropanolammonium tetracosyl sulfate; 2-hexanolammonium hexadecyl sulfate; 1-decanolammonium 2,7,8-trimethyldecyl sulfate; monoethanol ammonium nonyl sulfate; ammonium decyl sulfate; ammonium 2,3,5-trimethylhexyl sulfate; triethanolammonium octyl sulfate; n-dipentanolammonium octadecyl sulfate; 3-heptanolammonium nonyl sulfate, as well as the corresponding alkali metal (i.e. sodium and potassium) salts of these and other sulfates.

Although the preferred anionic detersive surfactants in the practice of this invention are the alkyl aryl sulfonates and the alkyl sulfates, other anionic detersive surfactants can also be used. For example, those sulfated oxyethylated phenols of the following general formula can be used:

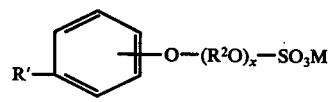

where R' is a straight or branched chain alkyl group having from about 5 to about 24 carbon atoms, $R^2$ is an alkyl radical containing from 2 to 4 carbon atoms, $x$ is an integer from 3 to 30 and M is either an alkali metal, ammonium or an alkanol substituted ammonium radical.

Compounds illustrative of the sulfated oxyethylated alkyl phenol class of anionic surface active agents useful in the practice of this invention include ammonium nonyl phenoxy tricosapropyleneoxy sulfate; triisopropanolammonium dodecylphenoxy hexadecaethyleneoxy sulfate; ammonium decylphenoxy tripropyleneoxy sulfate; monoethanolammonium octylphenoxy decabutyleneoxy sulfate; as well as 1-mono-decanolammonium hexylphenoxy tridecaethyleneoxy sulfate; triethanolammonium dodecylphenoxy eicosylpropyleneoxy sulfate; dibutanolammonium decylphenoxy cosabutyleneoxy sulfate; monoethanolammonium octylphenoxy hexaethyleneoxy sulfate; diethanolammonium tridecylphenoxy tetradecapropyleneoxy sulfate; monobutanolammonium tetradecylphenoxy heptapropyleneoxy sulfate; triethanolammonium cosylphenoxy octadecaethyleneoxy sulfate; and ethanolammonium dodecylphenoxy tridecabutyleneoxy sulfate; as well as the corresponding alkali metal salts of these and other similar sulfates.

Preferred sulfated oxyethylated alkylphenols include triethanolammonium dodecylphenoxy decaethyleneoxy sulfate; monoethanolammonium tetradecylphenoxy decapropyleneoxy sulfate; monoethanolammonium octylphenoxy pentaethyleneoxy sulfate; diisopropanolammonium octadecylphenoxy decaethyleneoxy sulfate; ammonium pentaeicosaethyleneoxy sulfate; monoethanolammonium tridecylphenoxy tridecaethyleneoxy sulfate; triethanolammonium tetradecylphenoxy decaethyleneoxy sulfate; triisopropanolammonium dodecylphenoxy octadecaethyleneoxy sulfate and the corresponding alkali metal compounds.

Other anionic detersive surfactants which can be used include the alkali metal, ammonium and alkanol substituted ammonium salts containing at most 10 carbon atoms of alkyl containing sulfosuccinic acid such as diamyl, dioctyl esters of sulfosuccinic acid. In addition, a number are described in Schwartz, Perry and Berch, Surface Active Agents and Detergents, Vol. II, Interscience Publishers, New York (1958).

The cation-active or cationic surface active agents are characterized by the fact that the hydrophobic group forms part of a cation when the compound is dissolved in water. The class may be regarded as consisting broadly of those bases which contain a typical hydrophobic group, and may be sub-classified according to the essential nature of the functional basic group. The amines and quaternary ammonium salts constitute by far the largest group of cationic surface active agents. Aside from the amines and quarternary ammonium compounds there is a group of nitrogeneous bases including guanidines, hydrazines, amine oxides, basic nitrogen heterocyclic substances, etc., around which surface active agents have been synthesized. Finally, there is the group of non-nitrogenous bases, of which the most noteworthy are the sulfonium compounds.

The cationic surfactants utilizable in this invention are of the type generally described in Schwartz, Perry and Berch, "Surface Active Agents and Detergents", Vol. II, pp. 103–119, Interscience Publishers, Inc., New York, (1958).

Non-ionic surfactants can be broadly described as compounds which do not ionize but acquire hydrophylic characteristics from an oxygenated side chain such as polyoxyethylene. The lyophilic part of the non-ionic surfactant molecule may come from fatty acids, phenol, alcohols, amides and amines. The non-ionic detersive surfactants are usually made by reacting an alkylene oxide such as ethylene oxide, butylene oxide, propylene oxide and the like with fatty acids, a straight or branched chain alcohol, phenols, thiophenols, amides and amines to form polyoxyalkylene glycol ethers and esters, polyoxyalkylene amides and the like. It is generally preferred to react from about 3 to about 30 moles of alkylene oxide per mole of the fatty acids, alcohols, phenols, thiophenols, amides or amines.

Illustrative of these non-ionic detersive surfactants are the products obtained from the reaction of alkylene oxide such as ethylene oxide and/or propylene oxide, with an aliphatic alcohol having from 8 to 18 carbon atoms, such as octyl, nonyl decyl, octadecyl, dodecyl, tetradecyl and the like; with an alkyl phenol in which the alkyl group contains between 4 and 20 carbon atoms, such as butyl, dibutyl, amyl octyl, dodecyl, tetradecyl and the like; with an alkyl amine in which the alkyl group contains between 1 to 8 carbon atoms; and with a fatty alkanol amide in which the alkyl group contains between 6 and 24 carbon atoms. Also the sugar esters, the mannitol esters and the sorbital esters. Phosphonium compounds may also be used.

Compounds illustrative of synthetic non-ionic surface-active agents include the products obtained from condensing from 3 to 30 moles of ethylene oxide or propylene oxide per mole of the following: propylene glycol, ethylene diamine, diethylene glycol, dodecyl phenol nonyl phenol, tetradecyl alcohol. N-octadecyl diethanolamide and N-dodecyl monoethanolamide. A number of non-ionic detersive surfactants are described in Schwartz, Perry and Berch, Surface Active Agents and Detergents, Vol. II, Interscience Publishers, New York (1958).

Builders and other additives such as corrosion inhibitors, perfumes, dyes, brightening agents, antiredepositon agents, etc., may also be included in the composition without affecting its primary purpose. An example of a builder which may be used in a finely divided sodium polyphosphate selected from the group consisting of sodium tripolyphosphate, tetrasodium pyrophosphate and mixtures thereof.

It is possible in a liquid detergent of this invention to incorporate an inorganic nonphosphate salt such as sodium sulfate. Additives, such as sodium carboxy methyl cellulose as an anti-redepositon agent, or anhydrous sodium silicate as corrosion inhibitor; and perfumes, dyes and brightening agents may also be added. The antiredeposition agents, corrosion inhibitors, perfumes, dyes and brightening agents, if used, are generally added in amounts of below about 10% by weight.

Illustrative of the use of the instant compounds in detergent compositions and the like are the following examples:

EXAMPLE 5

A liquid dishwashing compound was prepared according to the following formula:

| Components | Parts By Wt. |
| --- | --- |
| 2-coco-1-hydroxyethyl-1-imidazoline oxide (product of Example 3) | 10 |
| Triethanol amine "Lorol 5" sulfate (40% concentration) ("Lorol 5" is a DuPont mixture of fatty alcohols) | 10 |
| Sodium dodecyl benzene sulfonate (60% concentration) | 10 |
| Ethyl alcohol | 10 |
| Water | 60 |

The above components were thoroughly mixed at room temperature to form the liquid composition.

A similar composition may be prepared in the same manner, subsituting the 2-tallow-1-hydroxyethyl-1-imidazoline oxide of Example 4 for the imidazoline oxide of Example 3. A similar compound may also be made by the same procedure but substituting the aforesaid isopropylene-containing compounds for the ethylene-containing imidazoline oxides.

EXAMPLE 6

A heavy duty general purpose detergent was prepared by mixing in a sigma type tumble mixer, the following components;

| Components | Parts By Wt. |
| --- | --- |
| Sodium tripolyphosphate | 45 |
| Sodium sulfate | 25 |
| Sodium metasilicate | 5 |
| Sodium "Lorol 5" sulfate (90% concentration) | 5 |
| Sodium dodecyl benzene sulfonate (60% concentration) | 20 |
| 2-coco-1-hydroxyethyl-1-imidazoline oxide (product of Example 3) | 10 |

The electrolytes were tumbled, while being heated to about 80° C, or until most of the water was driven off, and the surface-active components were added gradually. As the water was driven off during the tumbling, a free-flowing powder remained.

The same procedure can be used to obtain a similar product but substititing the 2-tallow-1-hydroxyethyl-1-imidazoline oxide of Example 4. The same procedure can also be used while substituting the isopropylene-containing imidazoline oxides.

EXAMPLE 7

A liquid shampoo was prepared using the following components:

| Components | Parts by Wt. |
| --- | --- |
| Triethanolamine "Lorol 5" sulfate (40% concentration) | 30 |
| Triethanolamine laurate | 5 |
| 2-coco-1-hydroxyethyl-1-imidazoline oxide | |

| Components | Parts by Wt. |
| --- | --- |
| (product of Example 3) | 10 |
| Hexylene glycol | 10 |
| Water | 45 |

These components were mixed at room temperature to form the liquid shampoo.

Here again, the imidazoline oxide of Example 4 may be substituted for that of Example 3 or the corresponding isopropylene imidazoline oxides may be used instead of the ethylene-containing compounds.

EXAMPLE 8

A shampoo was prepared by mixing at room temperature, the following composition:

| Components | Parts by Wt. |
| --- | --- |
| Millmaster-Onyx "Maprofix ES" 30% (a sodium lauryl ether sulfate) | 40 |
| Amine oxide of Example 3 (or 4) | 10 |
| NaCl | 0.1 – 0.2 |
| Ethylene glycol | 2 |
| Perfume | 0.5 |
| Water | 47.3 |

EXAMPLE 9

A liquid dishwashing compound was prepared by mixing at room temperature, the following components:

| Components | Parts by Wt. |
| --- | --- |
| Millmaster-Onyx "Neutronyx S 60" (the ammonium salt of a sulfated alkylphenol polyglycol ether) 60% active | 30 |
| The amine oxide of Example 3 | 10 |
| Sodium xylene sulfonate, 40% | 5 |
| Water | 55 |

EXAMPLE 10

A bar soap was prepared using a 4:1 ratio of high-grade tallow-coconut oil saponified with caustic soda by a standard commercial process. It was finished to about 65% strength as fatty acid, and at low free alkali and salt content. The following mixture was milled, compressed, extruded and formed into bars of soap:

| Components | Parts by Wt. |
| --- | --- |
| Coconut-tallow soap | 65 |
| General Aniline & Film Corp. "Igepon AC 78", a coconut oil acid ester of sodium isethionate | 25 |
| The amine oxide of Example 3 | 10 |
| Perfume and color may be added if desired. | |

EXAMPLE 11

A heavy duty laundry detergent was prepared by mixing at room temperature the following components:

| Components | Parts by Wt. |
| --- | --- |
| Alkyl benzene sulfonate, 60% active | 20 |
| The amine oxide of Example 3 (or 4) | 11 |
| General Aniline & Film Corp.'s "GAFAC LO", a sodium salt of a complex organic phosphate ester, 88% active | 10 |
| Sodium tri-poly phosphate | 5 |
| Sodium xylene sulfonate, 40% active | 10 |
| Water | 44 |
| Color and perfume are optional additives. | |

EXAMPLE 12

| Components | Parts by Wt. |
| --- | --- |
| Alkylphenol polyglycol ether (9.5 E.O.) | 10 |
| Amine oxide of Example 3 (or 4) | 15 |
| Hexylene glycol | 3 |
| Water (odor and color optional) | 72 |

This mixture, prepared at ambient conditions, is a non-ionic dishwashing compound.

EXAMPLE 13

A non-ionic liquid hand soap was prepared by mixing at room temperature:

| Components | Parts by Wt. |
| --- | --- |
| Alkylphenyl polyglycol ether (11 mols E.O.) | 5 |
| Amine oxide of Example 3 (or 4) | 30 |
| Propylene glycol | 2 |
| Water | 63 |

EXAMPLE 14

A "waterless" hand cleanser was prepared in two parts, separately; then mixed:

| Part A | |
| --- | --- |
| Components | Parts by Wt. |
| Potash-rosin soap, 40% active | 30 |
| The amine oxide of Example 3 (or 4) | 20 |
| Water | 15 |

| Part B | |
| --- | --- |
| Components | Parts by Wt. |
| Deodorized kerosene | 30 |
| Polyethylene glycol 600 soybean fatty-acid ester | 5 |

Part B was added gradually to Part A with constant agitation at room temperature. The product was a clear viscous paste.

EXAMPLE 15

A detergent-sanitizer was prepared by mixing at room temperature the following components:

| Components | Parts by Wt. |
| --- | --- |
| Millmaster-Onyx "BTC 2125" (a mixture of alkyl dimethyl benzyl and alkyl dimethyl ethylbenzyl ammonium chlorides, 50:50, and 50% active) | 6 |
| Alkylphenyl polyglycol ether (11 E.O.) | 4 |
| Soda Ash | 2 |
| Sodium tripolyphosphate | 3 |
| The amine oxide of Example 3 (or 4) | 5 |
| Water | 80 |

Instead of "BTC 2125" an equivalent amount of lauryl dimethyl dichlorobenzyl ammonium chloride, dodecyl trimethyl ammonium chloride or dodecylbenzyl trimethyl ammonium chloride may be substituted.

The invention claimed is:

1. A surface-active composition consisting essentially of (a) a surface-actively effective amount of a mixture of compounds having the structure:

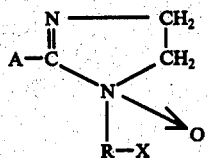

wherein A in any one given compound of said mixture represents one of the alkyl groups found in tallow fatty acids, R is either $C_2H_4$ or $C_3H_6$ and X is either OH or $NH_2$, and wherein the arrow indicates a semi-polar bond, (b) a detergently effective amount of a detergent selected from the group consisting of anionic, cationic and non-ionic detergents.

2. The composition of claim 1 wherein the proportion of (a) to (b) is from about 1:9 to about 6:1 by weight of the composition.

3. A method of cleaning and sanitizing an object which comprises applying to said object a composition consisting essentially of (a) a surface-actively effective amount of a mixture of compounds having the structure:

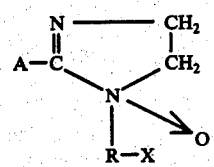

wherein A in any one given compounds of said mixture represents one of the alkyl groups found in tallow fatty acids, R is either $C_2H_4$ or $C_3H_6$ and X is either OH or $NH_2$ and wherein the arrow indicates a semi-polar bond, (b) a detergently effective amount of a detergent selected from the group consisting of anionic, cationic and non-ionic detergents.

4. The method of claim 3 wherein said detergent is present in a proportion of (a) to (b) of about 1:9 to about 6:1 by weight of the composition.

* * * * *